United States Patent [19]

Young

[11] 4,140,902
[45] Feb. 20, 1979

[54] DEVICE FOR MEASUREMENT OF HAIR-LIKE PARTICULATE MATERIAL

[75] Inventor: Robert A. Young, Chatsworth, Calif.
[73] Assignee: Xonics, Inc., Van Nuys, Calif.
[21] Appl. No.: 827,687
[22] Filed: Aug. 25, 1977
[51] Int. Cl.² ............................................. G01N 21/00
[52] U.S. Cl. .................................... 250/225; 356/339; 356/341
[58] Field of Search ................ 250/225; 356/103, 104, 356/114

[56] References Cited

U.S. PATENT DOCUMENTS 3,692,412   9/1972   Chubb .................................. 356/103

Primary Examiner—James B. Mullins
Attorney, Agent, or Firm—Harris, Kern, Wallen & Tinsley

[57] ABSTRACT

Apparatus for the measurement of hair-like particles, such as measurement of the amount of asbestos fiber in air. Apparatus including a source of a polarized beam of radiation directed to a scattering zone and a detector for detecting radiation of the beam scattered from the zone. A device at the zone, typically a pair of spaced parallel plates with an electric field therebetween, for orienting the hair-like particles parallel with each other and substantially perpendicular to the incoming beam of radiation, and a drive mechanism for rotating the polarized beam relative to the oriented particles to a first position with the polarization of the beam parallel to the particles and to a second position with the polarization of the beam perpendicular to the particles. A modulation reference signal and the signal from the radiation detector may be provided to a synchronous detector which produces an output varying as a function of the scattering produced by the hair-like particles and hence a function of the quantity of the particles in the zone. The scattering is much larger when the direction of the electric vector in the polarized beam is parallel to the long axis of the aligned hair-like particles.

14 Claims, 2 Drawing Figures

DEVICE FOR MEASUREMENT OF HAIR-LIKE PARTICULATE MATERIAL

BACKGROUND OF THE INVENTION

This invention relates to the measurement of small hair-like particles in a fluid, such as measurement of the amount of asbestos fiber in air. Asbestos fiber is in the order of 1/10 micron in diameter and of highly variable length, with the length always much greater than the diameter. It has been noted that the presence of asbestos fiber in air has an adverse affect on the health of people breathing the air and therefore simple and reliable equipment for measuring the amount of such fiber in air is desirable.

Accordingly, it is an object of the present invention to provide a new and improved apparatus for measuring hair-like particles in fluid, such as asbestos fiber in air, and to distinguish such hair-like particles from other geometrically different particles.

SUMMARY OF THE INVENTION

The scattering of electromagnetic radiation is governed by Maxwell's equations and certain boundary conditions. If the radiation is characterized by a wavelength $\lambda$ and a vector electric field $\bar{E}$, and if particles can be characterized by a smallest dimension d and a largest vector dimension $\bar{L}$, then maximum scattering occurs when $\bar{E}$ is parallel to $\bar{L}$ and when L is greater than $\lambda$. When $\bar{E}$ is perpendicular to $\bar{L}$, very little scattering will occur if d is less than $\lambda$.

In the apparatus of the invention the hair-like particles of a sample are oriented so that most are parallel to each other, radiation of a wavelength chosen to be less than the length of the particles and greater than the diameter is polarized and directed onto the oriented particles along a path perpendicular to the oriented particles, and the angular relation between the beam polarization and the particle orientation is changed between parallel and perpendicular. The radiation of the beam scattered by the particles to the detector will be a maximum when $\bar{E}$ is parallel to the particle orientation, and a minimum when it is perpendicular.

The apparatus of the invention includes a source of a polarized beam of radiation directed to a scattering zone along a first axis, a device for orienting hair-like particles parallel with each other and substantially perpendicular to the first axis in the zone, a drive for rotating the beam relative to the oriented particles to a first position with the polarization of the beam generally parallel to the particles and a second position with the polarization of the beam generally perpendicular to the particles, and a radiation detector for detecting scattered radiation from the zone. A synchronous detector having a radiation detector output and a reference signal as inputs may be used to provide an output varying as a function of the quantity of the hair-like particles in the zone.

DESCRIPTION OF THE PREFERRED EMBODIMENT

Figure 1:
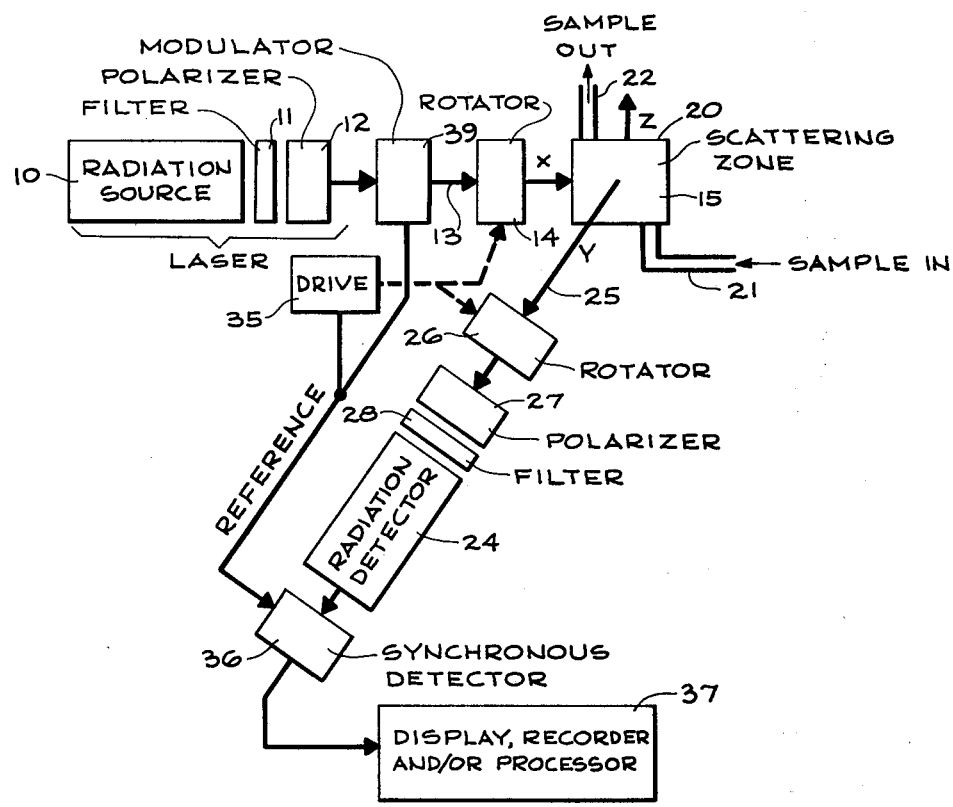
FIG. 1 is a diagram illustrating apparatus for the measurement of hair-like particles and incorporating the presently preferred embodiment of the invention.
Figure 2:
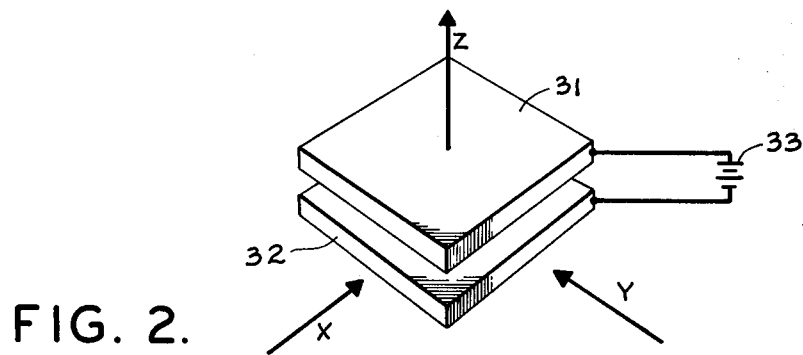
FIG. 2 illustrates a presently preferred apparatus for orienting the hair-like particles.

In the apparatus of FIG. 1, a radiation source 10 directs a beam of electromagnetic radiation through a filter 11 and a polarizer 12 along a path 13 past a polarization rotator 14 to a scattering zone 15. The scattering zone may be formed by a closed cell 20 with an input line 21 and an output line 22 for flowing a sample through the zone. Alternatively, the scattering zone may be an unconfined volume if background radiation or other interference is not present.

A radiation detector 24 provides for measurement of intensity of scattered radiation along a path 25 from the zone past a polarization rotator 26, a polarizer 27, and a filter 28.

The source 10 may be any source of electromagnetic radiation. The filter 11 limits the wavelength of the output to a relatively narrow band at the wavelength of interest, with the bandwidth preferably being in the order of 1/100 of the wavelength and with the wavelength selected to fall between the smallest dimension or diameter of the hair-like particles to be measured and the largest dimension or length of the particles. The polarizer 12 functions to filter out all emission whose $\bar{E}$ vector does not lie within a few degrees of a predetermined direction. Hence the beam of radiation at 13 is relatively narrow band and polarized. If desired, a laser, such as a helium-neon laser, with Brewster angle windows within the laser cavity and appropriately tuned cavity mirrors, can be utilized to provide the narrow band polarized beam.

Means are provided at the scattering zone for orienting the hair-like particles. This may be accomplished by utilizing parallel spaced plates 31, 32, with a voltage source 33 connected across the plates. The sample to be measured is positioned between the plates and the hair-like particles will be oriented by the electric field generally parallel with each other and perpendicular to the plates 31, 32. The sample may be exposed to ionization radiation or a Tesla discharge prior to being placed between the electrodes 31, 32 so that the particles in the sample become charged in order to enchance their orientation by the applied electric field.

The electrode plates 31, 32 are positioned with respect to the source 10 so that the oriented particles are perpendicular to the axis of the beam from the source. In the drawings, three mutually perpendicular axes X, Y and Z are illustrated with the beam from the radiation source aligned with the X axis and the oriented particles in the scattering zone parallel to the Z axis. The beam path 25 to the detector 24 desirably is in a plane perpendicular to the Z axis and preferably along the Y axis perpendicular to the X axis as well.

The polarization rotator 14 is actuated by a drive unit 35 and functions to move the polarization direction or $\bar{E}$ vector of the beam from a position parallel to the oriented particles to a position perpendicular to the oriented particles. The change may be continuous or step wise as desired. Various conventional polarization rotators are available and can be used. One example would be a quarter wave plate which would rotate the $\bar{E}$ vector by 90° when inserted into the optical path. The polarization rotator 26, polarizer 27 and the filter 28 correspond to the rotator 14, the polarizer 12 and the filter 11, respectively. The components 26, 27 and 28 will be preferred for most applications, but where there is no interfering light falling either on the particles or the detector, there will be no need for these components.

The radiation detector 24 is conventional and can be a photomultiplier or a solid state photo diode or a photo voltaic cell. The output from the detector is connected to a synchronous detector 36 which also has a reference signal from the drive unit 35. This synchronous detector may be conventional and may be analog or digital, providing an output suitable for display, recording and/or further processing at 37.

In operation, a sample is introduced into the zone between the electrodes 31, 32 and the applied field from the power source 33 orients the hair-like particles in the sample along the Z axis. Radiation from the source is directed into the zone and radiation scattered from the particles in the zone is detected. A scattering measurement is made with the beam polarization parallel to the particle orientation and with the beam polarization perpendicular to the particle orientation. Particles whose largest dimension L is in the order of their smallest dimension d, i.e., spherical or cubical particles, will show little polarization dependent scattering, producing substantially the same amount of scattering for both polarizations of the incident beam. However the hair-like particles will show a substantial difference in scattering and when all the hair-like particles are oriented parallel to each other, the difference in output for the two polarizations provides a measure of the quantity of such particles present in the sample. The synchronous detector functions to measure the difference in output for the two polarizations.

In the embodiment illustrated, the change in polarization is effected by the polarization rotator 14. In an alternative embodiment, the source including the filter and polarizer could be rotated relative to the scattering zone. In another alternative embodiment, the scattering zone and the detector could be rotated with the source remaining fixed.

The polarization rotator 26 operates to reverse the rotation of the rotator 14 so that the radiation from the source is always of appropriate polarization to pass the polarizer 27 at the input of the detector. The filter 28 is selected to match the bandwidth of the filter 11. These components serve to limit the input to the detector to scatter radiation from the source and reject other extraneous radiation.

In the operation described above for synchronous detection, the rotator 14 is operated at a rate to provide a modulaion frequency for the beam sufficiently high to use for synchronous detection. Alternatively, the polarization rotator rate may be much lower and beam modulation may be obtained with a separate modulator 39, which also provides the reference signal for synchronous detection.

I claim:

1. In an apparatus for measurement of hair-like particles, the combination of:
    first means for producing a polarized beam of radiation along a first axis directed to a zone;
    second means for orienting hair-like particles in said zone parallel with each other and substantially perpendicular to said first axis;
    third means for rotating said beam relative to said oriented particles to a first position with the polarization of said beam generally parallel to said particles and to a second position with the polarization of said beam generally perpendicular to said particles; and
    fourth means for detecting radiation of said beam scattered from said zone.

2. Apparatus as defined in claim 1 wherein said first means comprises a radiation source, a filter and a polarizer.

3. Apparatus as defined in claim 1 wherein said first means comprises a laser.

4. Apparatus as defined in claim 1 wherein said second means includes spaced parallel plates and means for connecting a voltage source across said plates, with said plates disposed parallel to said first axis.

5. Apparatus as defined in claim 1 including a sample cell enclosing said zone, and means for directing a sample through said cell.

6. Apparatus as defined in claim 1 wherein said third means includes a polarization rotator for positioning between said first means and said zone, and
    drive means for actuating said rotator to rotate said beam polarization from said first position to said second position.

7. Apparatus as defined in claim 6 including a second polarization rotator for positioning between said zone and said fourth means,
    with said drive means connected to said second polarization rotator for actuating both said rotators in synchronism.

8. Apparatus as defined in claim 1 wherein said fourth means includes a polarizer for limiting detected radiation to a predetermined polarization angle, and
    a filter for limiting detected radiation to a predetermined wavelength band.

9. Apparatus as defined in claim 1 with said first and fourth means positioned so that the beam path from said first means to said zone and the beam path from said zone to said fourth means lie in a plane substantially perpendicular to said oriented particles.

10. Apparatus as defined in claim 9 wherein said beam paths are substantially perpendicular to each other.

11. Apparatus as defined in claim 1 wherein the wavelength of said beam is greater than the diameter of said particles and less than the length thereof.

12. Apparatus as defined in claim 11 wherein the bandwidth of said beam is in the order of $10^{-2}$ the wavelength thereof.

13. Apparatus as defined in claim 1 wherein said third means includes means producing a reference signal varying as a function of the relative angular position of said beam polarization and particle orientation; and including
    synchronous detector means having the output of said fourth means and said reference signal as inputs and providing an output varying as a function of the quantity of said particles in said zone.

14. Apparatus as defined in claim 1 including a beam modulator for modulating said polarized beam along said first axis and producing a reference signal varying as a function of the modulation, and
    synchronous detector means having the output of said fourth means and said reference signal as inputs and providing an output varying as a function of the quantity of said particles in said zone.

* * * * *